Figure 1:
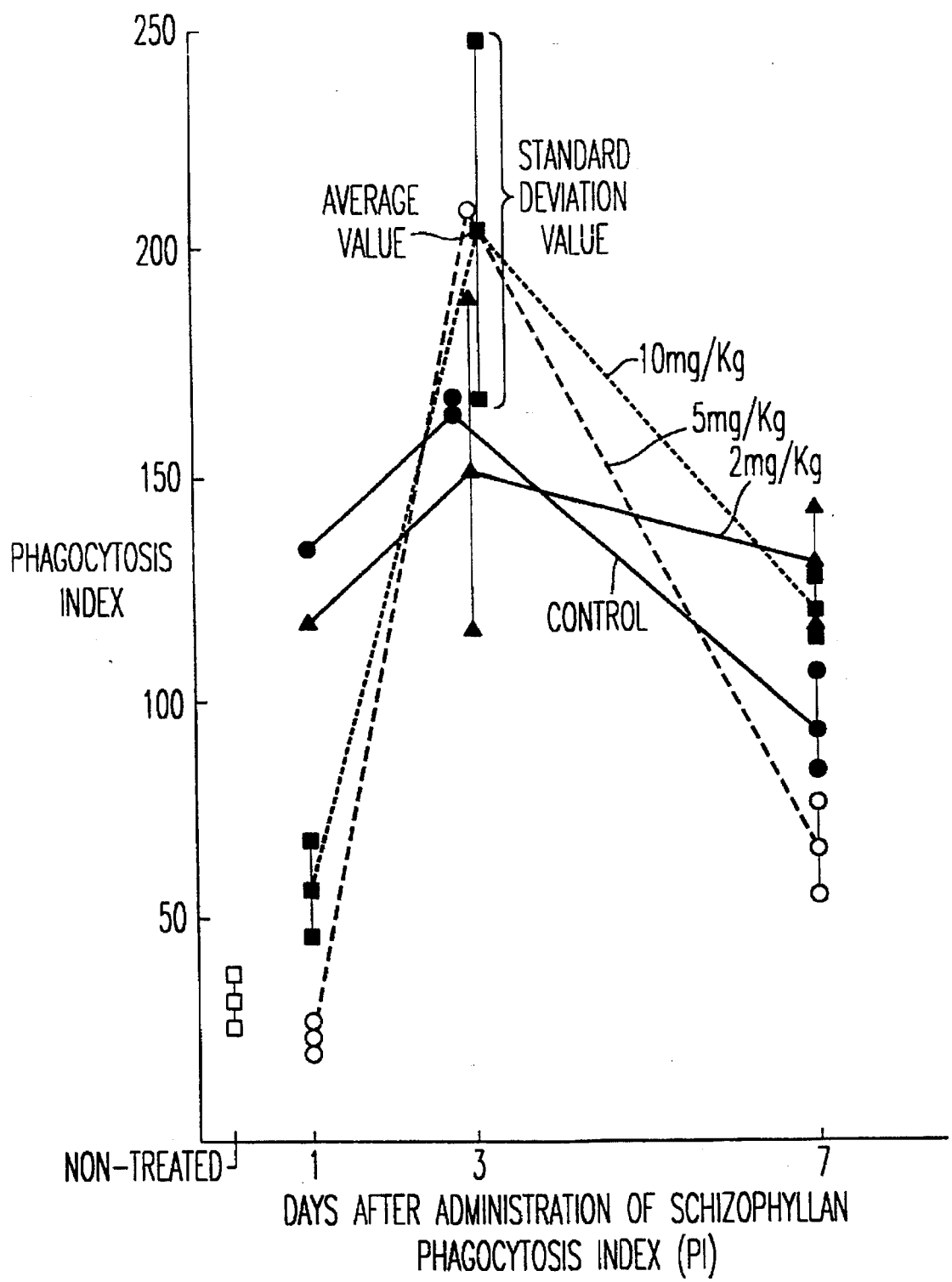

United States Patent [19]
Takahashi et al.

[11] Patent Number: 5,641,761
[45] Date of Patent: Jun. 24, 1997

[54] PREVENTIVE AGENT AGAINST INFECTIOUS DISEASE OF CRUSTACEA

[75] Inventors: Yukinori Takahashi; Toshiaki Itami, both of Shimonoseki, Japan

[73] Assignee: Taito Co., Ltd., Tokyo, Japan

[21] Appl. No.: 443,169

[22] Filed: May 17, 1995

Related U.S. Application Data

[60] Continuation of Ser. No. 109,253, Aug. 20, 1993, abandoned, which is a division of Ser. No. 831,197, Jan. 31, 1992, abandoned.

[30] Foreign Application Priority Data

Feb. 1, 1991 [JP] Japan ................. 3-012168

[51] Int. Cl.$^6$ ................................ A61K 31/715
[52] U.S. Cl. ................. 514/54; 426/2; 426/658; 536/123; 536/124; 536/1.11; 536/123.12
[58] Field of Search ................. 514/54; 536/123, 536/123.6, 124, 1.1; 426/2, 658

[56] References Cited

U.S. PATENT DOCUMENTS

| | | | |
|---|---|---|---|
| 3,943,247 | 3/1976 | Komatsu et al. | 424/180 |
| 5,032,401 | 7/1991 | Jamas et al. | 424/426 |
| 5,147,862 | 9/1992 | Niki et al. | 514/54 |
| 5,401,727 | 3/1995 | Rorstad et al. | 514/54 |

FOREIGN PATENT DOCUMENTS

| | | |
|---|---|---|
| 7933891 | 1/1992 | Australia. |
| 0384323 | 8/1990 | European Pat. Off.. |
| 0 466 037 A2 | 1/1992 | European Pat. Off.. |
| 60-45522 | 3/1985 | Japan. |

OTHER PUBLICATIONS

Japanese Application No. 2-218615 (Abstract).
British Veterinary Journal, (1995), vol. 151, pp. 45–69 "Vaccination in European Salmonid Aquaculture: A Review of Practices and Prospects".
Pathology in Marine Science (1990), pp. 465–469, "The Present State of Immunological Research in Marine Aquaculture".
Yano, CA113: 184712q (1990).

*Primary Examiner*—Jean C. Witz
*Attorney, Agent, or Firm*—Oblon, Spivak, McClelland, Maier & Neustadt, P.C.

[57] ABSTRACT

A preventive agent against infectious diseases of crustacea, which comprises a glucan having a main chain consisting essentially of beta-1,3-glucopyranosyl residues and/or mycelia of the glucan-producible fungus as an effective component.

11 Claims, 4 Drawing Sheets

PREVENTIVE AGENT AGAINST INFECTIOUS DISEASE OF CRUSTACEA

This application is a Continuation of application Ser. No. 08/109,253, filed on Aug. 20, 1993, now abandoned; which is a divisional of Ser. No. 07/831,197, filed on Jan. 31, 1992, abandoned.

The present invention relates to a preventive agent against an infectious disease of crustacea, a host-defense mechanism potentiating agent for crustacea, a feed, and a method for producing thereof, where the preventive agent, the host-defense mechanism potentiating agent, and the feed, contain a specific polysaccharide, a glucan (hereinafter simply referred to as "said glucan") consisting essentially of a main chain of beta-1,3-glucopyranosyl residues bearing beta-1,6-glucopyranose side chains.

It is known that polysaccharides extracted from various mushrooms enhance immune systems of mammals including mankind, and these polysaccharides are mainly exemplified by glucans consisting essentially of main chains of beta-1,3-glucopyranosyl residues bearing beta-1,6-branched glucopyranose side chains.

On the other hand, preventive methods using vaccines and curative methods using antibiotics are known to be effective against fish diseases. It is also known that FK-565 (see Japanese Unexamined Patent Publication No. 233923/1988) and said glucan (see Japanese Unexamined Patent Publication No. 218615/1990) exhibit preventive or curative effects against fish diseases depending on their immunopotentiating activities.

In order to highly utilize marine resources, various fishes and shellfishes are widely cultured recently. It is reported that in the aquacultural field, bacterial and viral infectious diseases of crustacea often occur resulting in a considerable loss of the harvest.

For preventing or treating these infectious diseases, a variety of pharmaceutical agents have been developed and used, the majority of which are antibiotics. The use of antibiotics, however, results in that pathogenic bacteria gains tolerance to the antibiotics and that intake of an antibiotic through eating antibiotic-administered crustacea leads a person to tolerance to the antibiotics. Thus, the use of antibiotics tends to be prohibited or regulated all over the world.

On the other hand, the use of a vaccine with dead mycelia of pathogenic bacteria is tried resulting in no significant effect. Thus, the effects of vaccines are desired to be enhanced.

Under these circumstances, the present inventors have researched on effective means for enhancing the effect of a vaccine or for potentiating the host defense mechanism of fish, and achieved the present invention. With reference to the fact that said glucan shows effects for preventing infectious diseases and enhancing the immune system, of fishes, and with expectation that said glucan exhibits a similar effects to crustacea, the present inventors performed the research to find the present invention.

The first invention resides in a vaccine effective against infectious diseases of crustacea, which contains an effective amount of said glucan and/or mycelium of the glucan-producing fungus as an active component. The vaccine contains mycelia of pathogenic bacteria as a base component together with said glucan to demonstrate their synergistic effect depending on the adjuvant activity of said glucan.

The second invention resides in an agent for enhancing the host-defense mechanism of crustacea, which contains an effective amount of said glucan and/or mycelium of the glucan-producing microorganism as an active component. The present inventors have found that said glucan enhances specifically the host-defense mechanism of crustacea, to prevent the crustacea from being infected by pathogenic bacteria or viruses.

The third invention resides in a feed for crustacea, which contains said glucan and/or mycelium of the glucan-producing microorganism as an effective component, preferably in a concentration of from 0.001 to 10% by weight. An effect for preventing infectious diseases can be achieved by supplying crustacea with said feed to enhance the host-defense mechanism.

The fourth invention resides in a method for preparing a feed having the above-mentioned effect.

Examples of infectious diseases of crustacea include vibrio diseases of Kuruma prawn (Penaeus japonicus), Giant tiger prawn (Penaeus monodon), White-leg shrimp, or the like; parasitic diseases of Epistylis sp., Soothamnium sp., or the like; mycotic infectious diseases of Lagenidium sp., Siropidium sp., or the like; and viral infectious diseases of Baculovirus penaei (BP), Monodon Baculovirus (MBV), Hepatopancreatic Parvo-like Virum (HPV), or the like.

Said glucan is a water-soluble glucan consisting essentially of a main chain of beta-1,3-glucopyranosyl residues, which is extracellularly elaborated in a culture broth of a specific Basidiomycetes or produced by extraction from a fruiting body of the Basidiomycetes. It is also known that said glucan is produced by microorganism other than Basidiomycete (see U.S. Pat. No. 1,061,043). Said glucan generally consists essentially of a main chain of beta-1,3-glucopyranosyl residues bearing beta-1,6-glucopyranose units. The presence of the side chains renders said glucan water-soluble.

Some water-insoluble glucans, such as curdlan and laminarin, which consist essentially of main chains of beta-1,3-glucopyranosyl residues without side chain are also known. The water-insoluble beta-1,3-glucans generally show lower biological activities in comparison with those of water-soluble beta-1,3-glucans. Thus, said glucan does not include such a water-insoluble beta-1,3-glucan. The activities of the water-insoluble beta-1,3-glucans can be enhanced when turned to water-soluble by chemical modifications. The chemically modified water-soluble beta-1,3-glucans belong to said glucan.

Said glucan preferably exemplified by schizophyllan (see Japanese Examined Patent Publication No. 37873/1971), scleroglucan (see U.S. Pat. No. 1,601,043) and lentinan which is produced by extraction from Lentinus edodes mushroom. It is noticed that yeast glucan and immunopotentiating mannan were also suggested to exhibit similar biological activities to that of said glucan. However, it was difficult to confirm evidently their effects against infectious diseases of crustacea, because of fluctuation of the experimental results.

Mycelium of the schizophyllan-producing fungus, *Schizophyllum commune* Fries, is known to contain water-insoluble glucans consisting essentially of main chains of beta-1,3-glucopyranosyl residues bearing beta-1,6-glucopyranose side chains, but the complicated structures of these insoluble glucans have not been elucidated (J. G. H. Wessels, et al. Biochimica et Biophysica Acta, 273, 346–358 [1972]). The water-insoluble beta-1,3-glucans in the mycelium of *Schizophyllum commune* Fries may have similar effects against the infectious diseases to that of said glucan because pulverized mycelium of the fungus shows preventive effect against crustacea infections. A typical example of the scleroglucan-producing fungus is *Sclerolum glucanicum*.

Examples of glucans which may be used in the present invention are listed in the following Table.

TABLE

| Source | Polysaccharide | Structure Main chain | Side chain | Branching degree* |
|---|---|---|---|---|
| *Lentinus edodes* | lentinan | β-(1→3)G | 1,6-branching | 1:3 |
| *Schizophyllum commune* | schizophyllan (M. wt. 40 × 10⁴) | β-(1→3)G | 1,6-branching | 1:3 |
| *Sclerotum glucanicum* | scleroglucan | β-(1→3)G | 1,6-branching | 1:3 |
| *Corilus versicolor* | P-SK | β-(1→3)G  β-(1→4)G | 1,6-branching (protein branching) | 1:3 |
| *Porio cocos* | pachyman pachymaran | β-(1→3)G  β-(1→3)G | (1,6-branching tr.) | |
| *Grifora umbellata* | glucan (water-soluble) | β-(1→3)G | 1,6-branching→ | 1:3 |
|  | glucan (alkali-soluble) | β-(1→3)G  β-(1→3)G | 6Gl→4Gl→ | |
| *Ganoderma applanatum* | G-2-β fraction α-glucan mannogalactan | β-(1→4)G | 1,6-branching α-1,6-branching | 1:4–5 |
| *Gancderma lucidum* | glucan (extracted with hot water) | β-(1→3)G | 1,6-:1,2 branching→ 4Gl | 1:3–4 |
|  | glucan | β-(1→3)G | | 1:4 |
| *Auricalaria auricua-judae* | glucan I (water-soluble) | β-(1→3)G | 1,6-branching | 2:3 |
|  | glucan II (water-insoluble) | β-(1→3)G | 1,6 branching | 3:4 |
|  | acidic polysaccharide | α-(1→3)M | β-GA,β-xyl | |
| *Volvariella volvaceae* | mannogalactan glucan (cold alkali) | α-(1→6)Ca  β-(1→3)G | α-M 1,6-branching | 1:4 |
| *Pholiota nameko* | mucilage polysaccharide | β-(1→3)G, Ca | protein (13%) | |
| *Saccharomyces cerevisiae* | glucan (Fr,HP2) mannan | β-(1→3)G α-(1→6)Man | →6Gl→ →2Ml→ | 1:18 |
| *Pestalotia sp* 815 | pestalotan | β-(1→3)G | 1,6-branching | 4:5 |
| *Alcaligenes faecalis* | curdlan | β-(1→3)G | | |
| *Streptcoccus salivarius* | α-1,3-glucan | β-(1→3)G | →6Gl→ | |

*The branching degree denotes the ratio (branching point:number of β-1,3-linkage)

EXAMPLE 1

Figure 2:
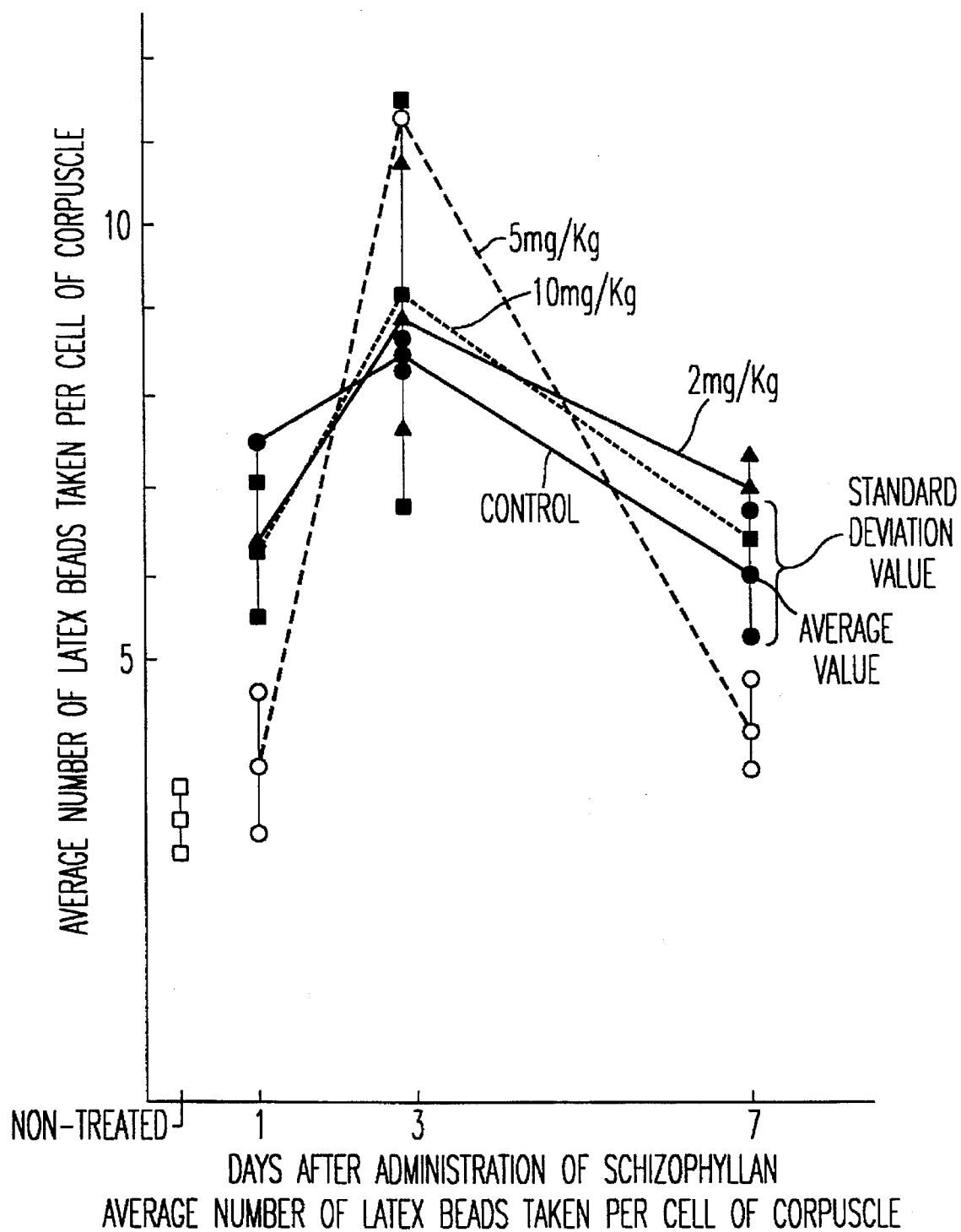

Kuruma prawns were divided into four groups each containing 20 prawns. Three groups were injected with physiological aqueous saline solution of schizophyllan at different dose levels of 10, 5 and 2 mg-schizophyllan/Kg-body weight. Control groups received saline. After 1, 3 and 7 days, blood was collected from the prawns and incubated with latex beads ($10^7$ beads of 0.8 micron diameter/ml-blood) in MEM culture medium, and phagocytosis of the beads into hemocyte was observed. N, number of beads phagocytized into 100 hemocytes and n, percentage of number of beads-phagocytizing hemocyte, were calculated, and the relationship between phagocytic index (PI) and average number of beads phagocytized in one hemocyte was delineated in FIGS. 1 and 2.

The prawns in the groups of the dose levels of 10 mg and 5 mg schizophyllan/Kg-body weight showed apparently higher host-defense activities in comparison with that of the control group.

$(PI)=(N/100)\times(n/100)\times100$

EXAMPLE 2

Figure 3:
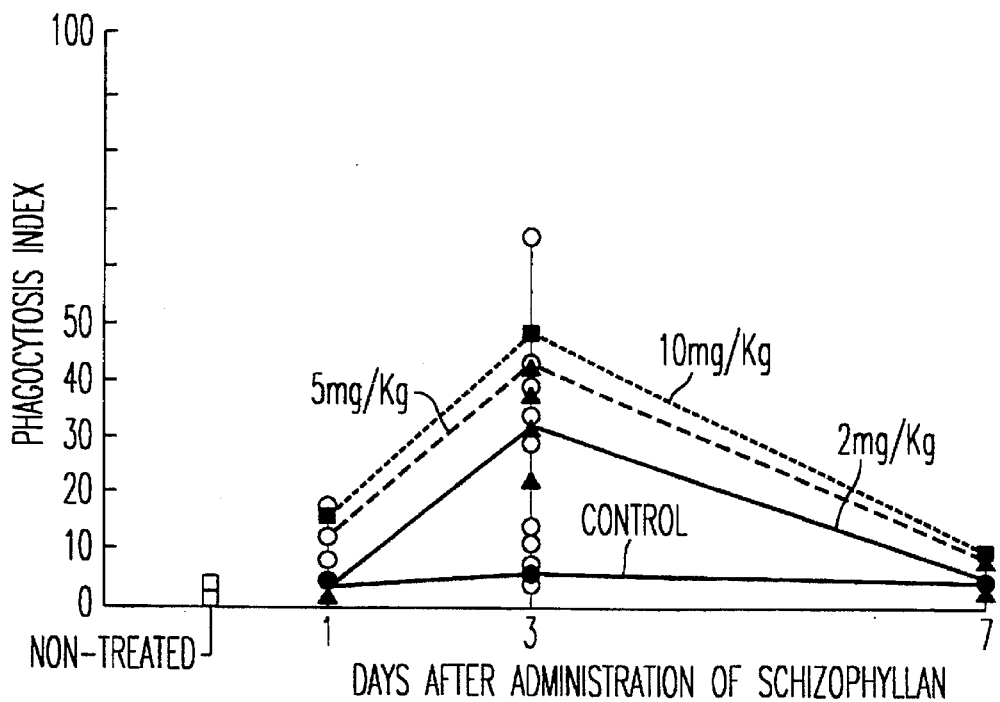
Figure 4:
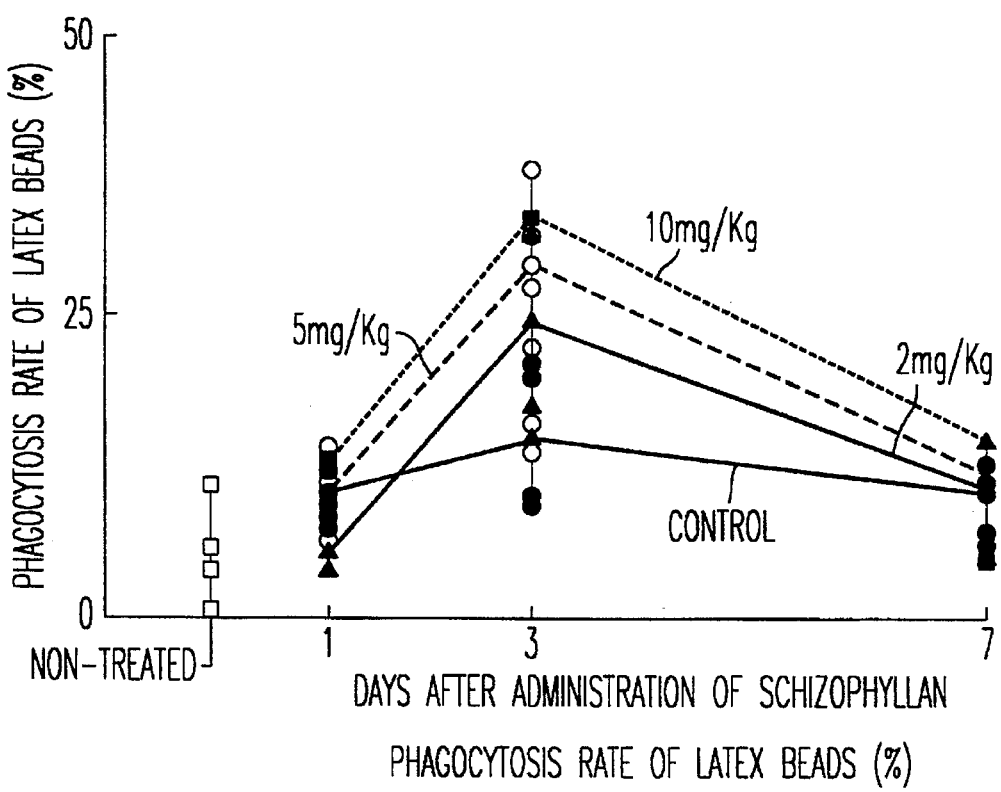

Kuruma prawns were divided into four groups of each 20 prawns. Schizophyllan was injected using physiological aqueous saline solution at different dose levels of 10, 5 and 2 mg-schizophyllan/Kg-body weight. Control group received saline. After 1, 3 and 7 days, $10^8$ latex beads were intramuscularly injected to each prawn. 45 Minutes after the beads-injection, the ratio of phagocytosis was determined and FIGS. 3 and 4 were obtained. Schizophyllan-administered groups showed apparently higher host-defense activities in comparison with the control group.

EXAMPLE 3

It is known that a prawn has a lymphatic organ (unknown organ) which plays an important role in the host-defense mechanism by phagocytizing foreign particles.

Kuruma prawns were divided into four groups of each 20 prawns, and the first group received i.m. injection of schizophyllan saline solution at a dose level of 10 mg/Kg-body weight, the second group, 5 mg/Kg-body weight, the third group, 2 mg/Kg-body weight, and the fourth group (control group), saline solution, followed by i.m. injection of $10^8$ latex beads/prawn. After 1, 3, 7 days, the lymphatic organs were extirpated, minced and spread on a slide glass. The number of the beads phagocytized per 1 mm² of the organ cells were counted.

Figure 5:
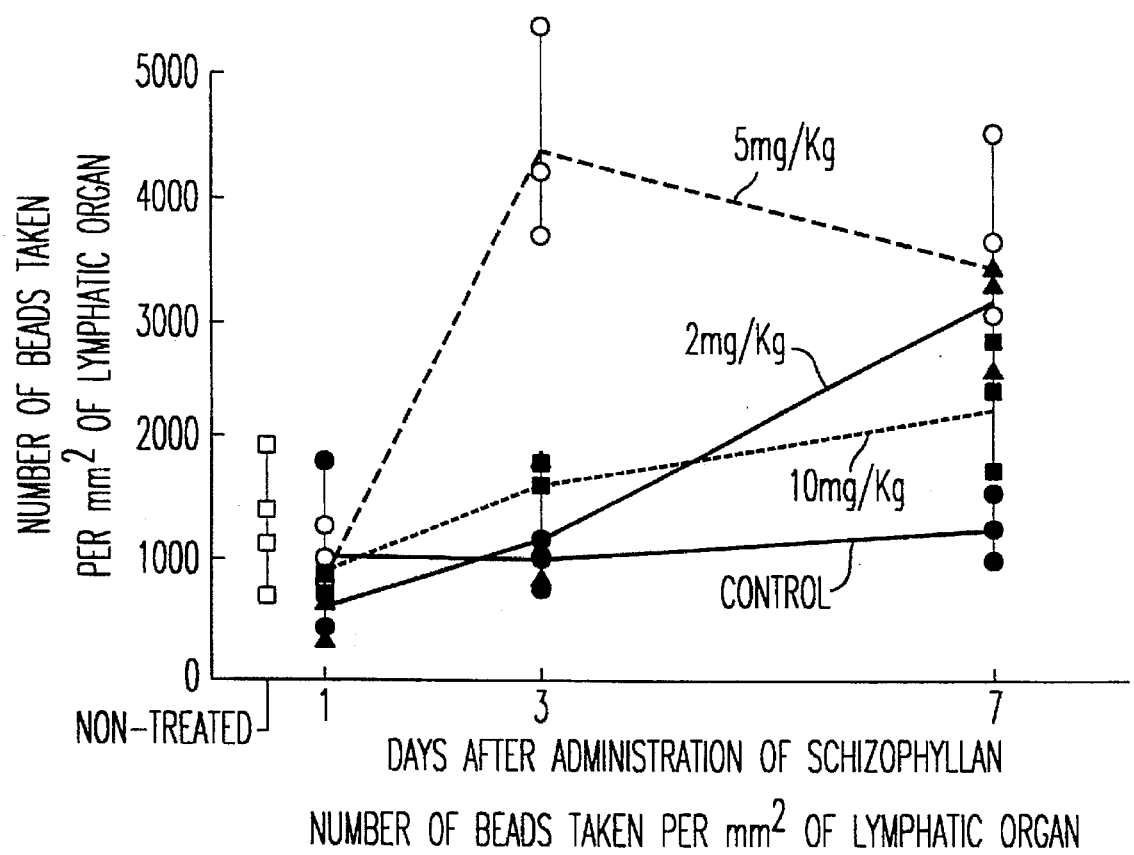

As shown in FIG. 5, the schizophyllan-administered groups showed higher beads-number phagocytized by the organ cells, indicating enhancement of the host-defense mechanism.

Preparation Example of Feed 0.2 to 2 g of schizophyllan was added to 1 kg of starting materials comprising fish meal, cuttlefish meal, cuttlefish-liver oil, beer yeast, various minerals, various vitamins, gluten, casein and α-starch, and was fully mixed therewith. An appropriate amount of water was added to the resultant mixture to form a paste. The paste was then charged into a feed extruding machine, and was extruded through an aperture of an internal diameter of 1.5 to 3.0 mm of the machine. The extruding temperature was about 85° to 95° C. and the extruding time was 10 to 20 minutes. The stringy feed thus extruded through the aperture of the machine was cut into a length of 5 to 12 mm suitable as a feed for prawns to obtain a final product.

The nutritive composition of the feed thus obtained comprised 50 to 60% of protein, 2.5 to 10% of fat, 2 to 4% of fiber and 15 to 20% of ash.

Preparation Example of Control Feed

Control feed was prepared in the same manner, except that schizophyllan was not contained.

EXAMPLE 4

Kuruma prawns were divided into two groups of each 20 prawns. One of the groups was fed with the above ordinary diet, while the other, with the same diet containing mycelia of schizophyllan-producible fungus so as to administer 10 mg of schizophyllan to each prawn a day.

After one month, the prawns were challenged by i.m. injection of virulent Vibrio sp.

One month after the challenge, the group administered with mycelia of schizophyllan-producible fungus showed 72% of the survival ratio, while the control group, 48% of the survival ratio.

EXAMPLE 5

The same test as in Example 1 was repeated by using scleroglucan in place of schizophyllan.

That is, Kuruma prawns were divided into four groups each containing 20 prawns. Three groups were injected with physiological aqueous saline solution of scleroglucan at different dose levels of 10, 5 and 2 mg-scleroglucan/Kg-body weight. Control groups received saline.

After 1, 3 and 7 days, blood was collected from the prawns and incubated with latex beads ($10^7$ beads of 0.8 micron diameter/ml-blood) in MEM culture medium, and phagocytosis of the beads into hemocyte was observed.

Phagocytic index (PI) and average number of beads phagocytized in one hemocyte were calculated in accordance with the equation described in Example 1, and the results were shown in Tables 1 and 2.

As evident from Tables 1 and 2, the prawns in the groups of the dose levels of 10 mg and 5 mg scleroglucan/Kg-body weight showed apparently higher host-defense activities in comparison with that of the control group.

TABLE 1

Changes in phagocytosis index in hemocyte cell of scleroglucan-administered Kuruma prawn

| Administration amount of scleroglucan | Days after administration of scleroglucan (days) | | |
|---|---|---|---|
| (mg/kg) | 1 | 3 | 7 |
| 2 | 95.3 ± 1.2 | 162.7 ± 22.2 | 123.1 ± 13.3 |
| 5 | 137.2 ± 9.5 | 195.4 ± 34.5 | 93.0 ± 12.0 |
| 10 | 125.8 ± 4.5 | 201.6 ± 14.6 | 87.9 ± 15.8 |
| Control | 112.5 ± 1.8 | 153.4 ± 2.5 | 65.6 ± 5.7 |

TABLE 2

Phagocytosis activity in hemocyte cel of scleroglucan-administered Kuruma prawn (Changes in average number of latex beads taken per cell of hemocyte)

| Administration amount of scleroglucan | Days after administration of scleroglucan (days) | | |
|---|---|---|---|
| (mg/kg) | 1 | 3 | 7 |
| 2 | 7.1 ± 3.6 | 8.0 ± 1.7 | 7.5 ± 0.9 |
| 5 | 5.9 ± 3.1 | 10.3 ± 2.6 | 4.2 ± 2.4 |
| 10 | 6.3 ± 4.2 | 9.2 ± 1.0 | 5.9 ± 3.8 |
| Control | 5.9 ± 1.9 | 6.7 ± 2.5 | 4.0 ± 2.3 |

EXAMPLE 6

In the same manner as in Example 5, Kuruma prawns were divided into four groups of each 20 prawns. Scleroglucan was injected using physiological aqueous saline solution at different dose levels of 10, 5 and 2 mg-scleroglucan/Kg-body weight. Control group received saline. After 1, 3 and 7 days, $10^8$ latex beads were intramuscularly injected to each prawn. 45 minutes after the beads-injection, the ratio of phagocytosis was determined in the same manner as in Example 5, and Tables 3 and 4 were obtained.

As evident from these Tables, scleroglucan-administered groups showed apparently higher host-defense activities in comparison with the control group.

TABLE 3

Changes in phagocytosis index in lymphatic organ of scleroglucan-administered Kumurama prawn

| Administration amount of scleroglucan | Days after administration of scleroglucan (days) | | |
|---|---|---|---|
| (mg/kg) | 1 | 3 | 7 |
| 2 | 10.6 ± 8.4 | 15.4 ± 14.3 | 7.0 ± 4.4 |
| 5 | 9.2 ± 2.4 | 28.9 ± 21.1 | 3.9 ± 0.9 |
| 10 | 18.2 ± 8.3 | 39.1 ± 17.8 | 6.8 ± 4.3 |
| Control | 9.3 ± 5.5 | 10.2 ± 5.4 | 3.2 ± 1.4 |

TABLE 4

Phagocytosis rate in lymphatic organ of scleroglucan-administered Kuruma prawn (Changes in average number of latex beads taken per cell of hemocyte)

| Administration amount of scleroglucan (mg/kg) | Days after administration of scleroglucan (days) | | |
|---|---|---|---|
| | 1 | 3 | 7 |
| 2 | 5.8 ± 3.8 | 20.6 ± 10.2 | 10.8 ± 4.4 |
| 5 | 11.2 ± 5.2 | 24.8 ± 8.5 | 13.3 ± 3.0 |
| 10 | 14.5 ± 4.1 | 30.1 ± 11.9 | 20.5 ± 8.6 |
| Control | 8.7 ± 2.5 | 10.1 ± 6.7 | 11.2 ± 4.3 |

EXAMPLE 7

In the same manner as in Example 3, Kuruma prawns were divided into four groups of each 20 prawns, and the first group received i.m. injection of scleroglucan saline solution at dose level of 10 mg/Kg-body weight, the second group, 5 mg/kg-body weight, the third group, 2 mg/Kg-body weight, and the fourth group (control group), saline solution, followed by i.m. injection of $10^8$ latex beads/prawn. After 1, 3, 7 days, the lymphatic organs were extirpated, minced and spread on a slide glass. The number of the beads phagocytized per 1 mm$^2$ of the organ cell were counted.

As shown in Table 5, the scleroglucan-administered groups showed higher beads-number phagocytized by the organ cells, indicating enhancement of the host-defense mechanism.

TABLE 5

Phagocytosis activity in lymphatic organ of scleroglucan-administered Kuruma prawn (Changes in average number of latex beads taken per mm$^2$ in lymphatic organ of scleroglucan-administered Kuruma prawn)

| Administration amount of scleroglucan (mg/kg) | Days after administration of scleroglucan (days) | | |
|---|---|---|---|
| | 1 | 3 | 7 |
| 2 | 1035.0 ± 240.6 | 1182.7 ± 609.6 | 2235.6 ± 1745.6 |
| 5 | 1214.7 ± 864.0 | 3995.2 ± 2408.5 | 2797.7 ± 870.3 |
| 10 | 1056.1 ± 665.4 | 1533.8 ± 1065.5 | 1775.2 ± 349.5 |
| Control | 1016.0 ± 388.8 | 998.8 ± 749.6 | 1089.0 ± 419.4 |

Preparation Example of Feed Containing Mycelia of Scleroglucan-Producible Fungus 0.2 to 3 g of mycelia of scleroglucan-producible fungus was added to 1 kg of starting materials comprising fish meal, cuttlefish meal, cuttlefish-liver oil, beer yeast, various minerals, various vitamins gluten, casein and α-starch, and was fully mixed therewith. An appropriate amount of water was added to the resultant mixture to form a paste. The paste was then charged into a feed extruding machine, and was extruded through an aperture of an internal diameter of 1.5 to 3.0 mm of the machine. The extruding temperature was about 85° to 95° C. and the extruding time was 10 to 20 minutes. The stringy feed thus extruded through the aperture of the machine was cut into a length of 5 to 12 mm suitable as a feed for prawns to obtain a final product.

The nutritive composition of the feed thus obtained comprised 40 to 60% of protein, 2.0 to 10% of fat, 2 to 5% of fiber and 10 to 20% of ash.

Preparation Example of Control Feed

Control feed was prepared in the same manner, except that mycelia of scleroglucan-producible fungus was not contained.

EXAMPLE 8

In the same manner as in Example 4, Kuruma prawns were divided into two groups of each 20 prawns. One of the groups was fed with the above ordinary diet, while the other, with the same diet containing mycelia of scleroglucan-producible fungus so as to administer 10 mg of scleroglucan to each prawn a day.

After one month, the prawns were challenged by i.m. injection of virulent Vibrio sp.

One month after the challenge, the group administered with mycelia of scleroglucan-producible fungus showed 65% of the survival ratio, while the control group 30% of the survival ratio.

We claim:

1. A method for enhancing the immune system of crustacea comprising the steps of:

feeding crustacea a food composition containing an effective amount of a water-soluble schizophyllan and mycelia of a schizophyllan-producing fungus.

2. The method of claim 1, wherein the content of said schizophyllan and said mycelia in the feed each ranges from 0.001 to 10% by weight.

3. The method of claim 1, wherein the feed further comprises 40 to 60% by weight of protein, 2.0 to 10% by weight of fat, 2 to 5% by weight of fiber and 10 to 20% by weight of ash.

4. A method for treating infections in crustacea selected from the group consisting of vibrio infections, mycotic infections and viral infections comprising the steps of:

feeding crustacea a food composition containing an effective amount of a water-soluble schizophyllan and mycelia of a schizophyllan-producing fungus.

5. The method of claim 4, wherein the content of said schizophyllan and said mycelia in the feed each ranges from 0.001 to 10% by weight.

6. The method of claim 4, wherein the feed further comprises 40 to 60% by weight of protein, 2.0 to 10% by weight of fat, 2 to 5% by weight of fiber and 20 to 20% by weight of ash.

7. A method for enhancing the immune system of crustacea comprising the steps of:

feeding crustacea a food composition containing an effective amount of a culture broth powder comprising 40±5 wt % of a water soluble schizophyllan and 60±5 wt % of mycelia of a schizophyllan-producing fungus.

8. The method of claim 7, wherein the content of said schizophyllan and said mycelia in the feed each ranges from 0.001 to 10% by weight.

9. The method of claim 7, wherein the feed further comprises 40 to 60% by weight of protein, 2.0 to 10% by weight of fat, 2 to 5% by weight of fiber and 10 to 20% by weight of ash.

10. A method for treating infections in crustacea selected from the group consisting of vibrio infections, mycotic infections and viral infections comprising the steps of:

feeding crustacea a food composition containing an effective amount of a culture broth powder comprising 40±5 wt. % of a water-soluble schizophyllan and 60±5 wt. % of mycelia of a schizophyllan-producing fungus.

11. The method of claim 10, wherein the content of said schizophyllan and said mycelia in the feed each ranges from 0.001 to 10% by weight.

* * * * *